United States Patent
Rajendran et al.

(10) Patent No.: US 9,327,006 B2
(45) Date of Patent: May 3, 2016

(54) EXTRACTION OF B-VITAMINS FROM PLANT MATTER

(76) Inventors: Ramaswamy Rajendran, Bangalore (IN); Kamala Rajendran, Bangalore (IN)

( * ) Notice: Subject to any disclaimer, the term of this patent is extended or adjusted under 35 U.S.C. 154(b) by 137 days.

(21) Appl. No.: 14/131,262

(22) PCT Filed: Jul. 30, 2012

(86) PCT No.: PCT/IN2012/000528
§ 371 (c)(1),
(2), (4) Date: Jan. 7, 2014

(87) PCT Pub. No.: WO2013/018103
PCT Pub. Date: Feb. 7, 2013

(65) Prior Publication Data
US 2014/0141107 A1    May 22, 2014

(30) Foreign Application Priority Data
Aug. 4, 2011  (IN) ........................... 2678/CHE/2011

(51) Int. Cl.
| | |
|---|---|
| *A01N 65/00* | (2009.01) |
| *A61K 36/752* | (2006.01) |
| *C07D 475/06* | (2006.01) |
| *A61K 36/53* | (2006.01) |
| *A61K 36/61* | (2006.01) |

(52) U.S. Cl.
CPC .............. *A61K 36/752* (2013.01); *A61K 36/53* (2013.01); *A61K 36/61* (2013.01); *C07D 475/06* (2013.01)

(58) Field of Classification Search
CPC .................................................... A61K 36/00
USPC ......................................................... 424/725
See application file for complete search history.

(56) References Cited

U.S. PATENT DOCUMENTS

| | | |
|---|---|---|
| 6,124,268 A | 9/2000 | Ghosal |
| 7,736,675 B2 | 6/2010 | Oben |
| 8,465,781 B2 | 6/2013 | Autzen et al. |
| 2013/0217768 A1 | 8/2013 | Nahas et al. |

FOREIGN PATENT DOCUMENTS

| | | |
|---|---|---|
| EP | 0020029 B1 | 2/1985 |
| WO | 2010/034971 A2 | 4/2010 |
| WO | 2011/103843 A1 | 9/2011 |

OTHER PUBLICATIONS

"Supercritical fluid extraction and fractionation of natural matter", Reverchon, et al., "The Journal of Supercritical Fluids" 38:146-166 (2006).

*Primary Examiner* — Michael Meller
(74) *Attorney, Agent, or Firm* — Robert E. Bushnell, Esq.

(57) ABSTRACT

A process for the extraction of the B group of vitamins from a first plant matter is disclosed wherein, prior to the said extraction operation, the first plant matter is treated with a second plant matter comprising acidic compounds. The acidification converts the vitamins into more water-soluble forms and increases the yield thereof. In one example, the first plant matter comprises guava fruit matter, holy basil leaves and lemon peels, the two last-mentioned plant species being the source of the acidic compounds. The vitamins extracted and the proportions thereof may be controlled by suitable choice of the plant species constituting the first and second plant matters and their quantities, such as to give a substantially ready formulation conforming to RDA values or other requirements. The vitamins extracted are B1, B2, B3, B5, B6 and B9, the above combination of plant matters giving a higher yield than others. The process is of general applicability to other plant constituents.

11 Claims, No Drawings

EXTRACTION OF B-VITAMINS FROM PLANT MATTER

CLAIM OF PRIORITY

Applicants are submitting these papers pursuant to §1893, of the Manual of PEP for entry of the national stage of the following PCT application, and this application makes reference to, incorporates the same herein, and claims all benefits accruing under 35 U.S.C. 365(c) of the PCT International application entitled EXTRACTION OF B-VITAMINS FROM PLANT MATTER filed on 30 Jul. 2012 and duly assigned Serial No. PCT/IN2012/000528 and makes reference to, incorporates the same herein and claims all benefits under 35 U.S.C. 119 from applications filed in the Indian Intellectual Property Office on 4 Aug. 2011 and there duly assigned Serial No. 2678/CHE/2011.

BACKGROUND OF THE INVENTION

1. Field of the Invention

This invention relates to a process of extraction of the B group of vitamins and other nutrients from plant matter and more particularly to a process of extraction of the B group of vitamins and other nutrients from plant matter by using water as solvent, wherein a first plant matter to be extracted is treated with one or more acidic compounds such as to convert one or more of the said B vitamins into forms thereof that are more water-soluble, said treatment of the said first plant matter with acidic compounds being carried out either before or during the said extraction thereof by water.

The B group of vitamins comprises the following:
(i) Vitamin B1—Thiamin
(ii) Vitamin B2—Riboflavin
(iii) Vitamin B3—Niacin
(iv) Vitamin B5—Pantothenic acid
(v) Vitamin B6—Pyridoxine
(vi) Vitamin B9—Folic acid
(vii) Vitamin B12—Cyanocobalamin

2. Approaches of the Related Art

The B group vitamins are water-soluble. However, their solubility in water is low and it varies considerably from one member of the group to another. Prior art processes of extraction of the B group of vitamins from plant matter often employ water as the solvent. Because of these factors, the extraction of the B vitamins in prior art processes is inefficient and is not uniform among the members of the group. The rate of extraction is also low.

Another feature of prior art processes for the extraction of the B group of vitamins from plant matter has been that the desired vitamins, minerals and other nutrients are first produced in isolated condition, only to be subsequently compounded to give desired mixtures. For example, individually isolated members of the B group of vitamins may be admixed to form a desired combination of nutrients in a formulation comprising a set of the B vitamins. This is energy intensive and requires numerous processing steps. There is a need in the art to improve the efficiency of the extraction of B group vitamins from plant matter by increasing the solubility of the B group vitamins in water and by reducing the number of necessary processing steps.

SUMMARY OF THE INVENTION

The present invention meets this need. The process of the invention provides increased yields of B group vitamins in extracts from suitable plant matter(s) and increased rates of dissolution of the said vitamins in the extracting solvent, addressing prior art limitations with respect to extractions of B group vitamins that employ water as the extraction solvent. That is, in contrast to the prior art, the extraction process is faster in the process of the invention and the yield is greater.

In the process of the invention, the solubilities of one or more of the B vitamins of the group are enhanced by conversion thereof into more water-soluble forms. Said conversion is carried out by treatment of the said first plant matter containing the B vitamins with one or more acidic compounds. The acidification converts them into forms that are more readily soluble in water. Such forms are salts, esters, alcohols and others. The scope of the terms 'acidic compounds', 'acidic constituents' and 'acidic components' is intended herein to include both free acids and compounds that are not free acids but are acidic.

The acidic compounds used in the process of the present invention may be any of the mineral acids such as hydrochloric, sulphuric, nitric, phosphoric, or others. Preferably, they are organic acids such as succinic, citric, tartaric, acetic, ascorbic, or others. Within the scope of the invention, the acidic compounds may comprise compounds other than free acids. The compound(s) used in the treating step may be mixtures of free acids and other acidic compounds within the scope of the invention.

More preferably, the organic acids adopted for said treatment are in the form of one or more plant matter(s), that is, plant matter(s) that comprises inherent acidic compounds, such as for example, lemon peels containing citric and ascorbic acids, or amla fruit matter containing ascorbic acid, or others. The acidic compounds may be either free acids or otherwise, or combinations of the two. The plant matter(s) containing the acidic compounds selected for treatment of the B vitamins and other nutrients is referred to herein as the second plant matter(s).

Accordingly, one object of the present invention is to provide a process for the extraction of B vitamins from plant matter that offers an increased yield in comparison with prior art processes.

Another object of the present invention is to provide a process for the extraction of B vitamins from plant matter that offers decreased processing times in comparison with prior art processes.

Another object of the present invention is to provide a process for the extraction of B vitamins from plant matter that provides a desired extracted vitamin mixture by means of a decreased number of processing steps in comparison with prior art processes.

Another object of the present invention is to provide a process for the extraction of B vitamins from plant matter that makes possible better capacity utilization for an existing manufacturing facility producing a desired B vitamin extract mixture.

Another object of the present invention is to provide a process for the extraction of B vitamins from plant matter that offers the opportunity for reduced operational and capital costs by means of appropriate selection of the first and second plant matters.

Another object of the present invention is to provide a process for the extraction of B vitamins from plant matter that offers enhanced extraction of desired B vitamins while suppressing extraction of other vitamin and mineral components of the plant matter(s) that are not desired.

Another object of the present invention is to provide a process for the extraction of B vitamins from plant matter that may be tailored to provide a desired B vitamin extract mixture without need to extract and/or isolate individual B vitamin components separately.

In certain embodiments, the present invention includes extractions of B group vitamins and other nutrients and constituents from plant matter(s) in which the nature and proportions of the first plant matter(s) and the second plant matter(s) with its acidic constituents may be selected in such a way as to provide an extract comprising B group vitamins, the B group vitamins in the extract being present in desired proportions. For example, such proportions may be those of the Recommended. Daily Allowance (RDA) values, U.S. Food and Drug Administration Daily Values, or other medical, nutritional, or therapeutic standards established by a governmental or professional body. Thus, the present invention addresses the limitation in the prior art requiring the energy intensive extra processing steps involved in isolating individual B group vitamins and subsequently admixing them to produce a desired product mixture of B group vitamins. The present invention allows for the preparation of a desired nutrient mixture with less manipulation and with fewer processing steps.

Attention is drawn to the co-pending Indian application for patent No. 2677/CHE/2011, filed 4 Aug. 2011, now U.S. patent application Ser. No. 14/131,326, by the present applicants/inventors, wherein a process for the extraction of plant matter is disclosed. In the disclosed process, a first plant matter, the plant matter to be extracted, is treated with a second plant matter that comprises acidic constituents. The first and second plant matters are brought into contact for the purposes of said treatment and accompanying reactions, either before or during the extraction thereof by water. The disclosure of U.S. patent application Ser. No. 14/131,326 is hereby incorporated by reference into the present application.

During said contact, the said acidic component(s) may react with the vitamin and mineral components of the first plant matter converting one or more of the water-soluble vitamins and minerals therein into more water-soluble forms and/or one or more of the water-insoluble vitamins and minerals therein into water-soluble forms. The water-soluble forms and more water-soluble forms may comprise salts, esters and other compounds resulting from the reaction(s) of the vitamins and mineral constituent(s) of the first plant matter with the acidic constituents contained in the second plant matter.

For example, one or more of the fat-soluble but water-insoluble vitamins A, D, E and K may be converted into water soluble forms in the process of the invention. Similarly, one or more of the other water-insoluble vitamin and mineral constituents therein may also be converted into soluble forms. Said acidic treatment of the invention may also convert some water-soluble nutrient(s) therein into forms that are more water-soluble.

Thus, one highlight of the process disclosed therein is that it may thereby be able to extract substantially all of the desired vitamins and minerals by means of a single solvent, namely, water. Another highlight is that in the process of the invention, this may be done in a single extraction operation. An extraction operation may, however, comprise a plurality of stages within the scope of the invention. The vitamins and minerals and other food and medicinal constituents of plants are referred to therein, and also herein, by the generalised term 'nutrients'. Said acidic treatment also enhances extractability, and the yields are observed to be higher than in prior art procedures.

It may be noted that the scope of the process of the invention is applicable to any of the nutrients or plant constituents and is not limited to B vitamins.

The process of the present invention may allow for the selection of acidic components such that all of the desired vitamins and minerals are obtained in the extract through a single extraction step with a single extraction solvent. Other synergies and cost benefits such as better yields, shorter processing times and others may also be realised. Thus, within the scope of the invention, the second plant matter may comprise a mixture of plant species selected in such a way as to give a spread of said acidic components leading to higher yields and said synergies and cost benefits.

In the present specification, an extraction may comprise a single extraction stage or a plurality thereof.

The objects of the invention and the advantages thereof are indicated at different points in the specification. Other objects and advantages will be apparent from the description and claims.

According to the invention, therefore, there may be provided a process for the extraction of B-vitamins and other nutrients and constituents from plant matter(s), comprising:
  (i) providing one or more first plant matter(s) containing one or more of the B-vitamins and other nutrients desired to be extracted;
  (ii) treating the said first plant matter(s) with one or more acidic compound(s) to render one or more of the B-vitamin components and nutrients that are water-soluble into form(s) that are more water-soluble, and/or to render one or more of the B-vitamin components and nutrients that are water-insoluble into form(s) that are water-soluble; and
  (iii) extracting the mixture of the first plant matter(s) and the one or more acidic compounds with water or a dilute aqueous extract solution, the dilute aqueous extract being a first extract solution from at least one previously conducted extraction process.

In certain embodiments, the process of the present invention may include treatment of the first plant matter(s) with a second plant matter(s), the second plant matter(s) comprising the one or more acidic compound(s) for the treatment of the first plant matter(s).

In certain embodiments, the second plant matter(s) of the process of the present invention may comprise one or more of the B group of vitamins and nutrients and may perform a dual role in the process by being a source of both acidic compound(s) and the one or more of the B group of vitamins and nutrients.

In certain embodiments, the first plant matter(s) of the process of the present invention may comprise one or more acidic compound(s) and may perform a dual role in the process by being both a source of one or more B group vitamins and a source of one or more acidic compound(s).

In certain embodiments, the treating and extracting steps of the process of the present invention may be carried out substantially simultaneously by dispersing (slurrying) the first and second plant matter(s) in the water solvent.

In certain embodiments, the treating step of the process of the present invention may comprise pulping the first and second plant matter(s), contacting the two plant matters in their pulped forms for a length of time, and subsequently contacting the contacted two plant matter(s) with the water solvent.

In certain embodiments, the treating step of the process of the present invention may comprise converting the first and second plant matters into powder forms.

In certain embodiments, the process of the present invention may include subjecting the first and second plant matter(s) to one or more preparatory operations selected from the group consisting of washing, cleaning, dicing, cutting, drying, crushing, grinding, milling, screening and blanching.

In certain embodiments, the process of the present invention may further include removing the solvent from an extract solution product produced by the process to yield a concentrated product; removing the solvent from an extract solution product produced by the process to yield a solid or semi-solid extract product; drying the extract product produced by the process to yield a solid form extract product and subjecting the product to at least one finishing operation selected from the group consisting of powdering, sieving, sifting, mixing and homogenizing; producing a solid form extract by adsorbing an extract product produced by the process on a suitable excipient and adopting a suitable binder as required; converting the extract into any of the known dosage forms; converting the B group of vitamins and other nutrients in an extract product produced by the process into any of the known pharmaceutically acceptable salts; adopting any of the known pharmaceutical carriers for the B vitamins and other nutrients of an extract product produced by the process; incorporating additives for one or more of color, texture, taste, flavour, bulk and odor in an extract product produced by the process; topping-up of one or more B vitamins and other nutrients and constituents and/or addition of one or more other B vitamins or nutrients to bring the extract into correspondence with a desired standard or specification; and performing a supplemental process or procedure for enhancing the efficacy or assimilability or one or more of the B vitamins and other nutrients in an extract product produced by the process.

In certain embodiments, the present invention may include an extract product produced by the process of the invention.

DETAILED DESCRIPTION OF THE INVENTION

Thus, in certain embodiments, the present invention includes the extraction of a mixture of a first plant matter comprising desired vitamins and/or minerals, such as one or more B vitamins, and one or more acidic compound(s) which may be comprised by a second plant matter. In preferred embodiments, the extraction may advantageously be carried out using water or dilute aqueous extracts from previous extraction steps as the extraction solvent.

The invention offers a wide scope for selecting said first and second plant matters such that the desired B vitamins and other plant nutrients as applicable are extracted in the optimum manner. The invention offers several cost benefits such as, for example, increased yield, decreased processing times, reduced handling of materials, better capacity utilisation and reduced operational and capital costs through the appropriate selection of the first and second plant matters, considering the nutrients and acidic components therein.

The invention also offers the option of selecting the above-mentioned parameters. The nature and proportions of the first plant matter(s) and the second plant matter(s) and the acidic constituents thereof may be selected so as to yield a nutrient mixture, for example, a mixture of the B vitamins wherein the proportions of the target nutrients are substantially the same as those required for administration to subjects for particular treatments, symptoms or nutritional requirements.

Such proportions may be such as those laid down as RDA (Recommended Daily Allowance) values or other authorities as required by health, medical or other considerations. It will be seen that obtaining the vitamin mixture (or other nutrient mixture) in desired therapeutic or nutritional proportions right at the conclusion of the extraction step eliminates a considerable amount of processing that is required in prior art processes. In prior art processes, the vitamins, minerals and other said nutrients are first produced in isolated condition only to be subsequently compounded to give the desired mixtures.

A variety of organic acids are available in plant matters. Within the scope of the invention, the first and second plant matters may be a mixture of plant matters of different species. This provides the option of selecting a combination of vitamin B and other nutrient sources and of said acidic compounds, such as to optimise the extraction in terms of the yields, the range of the nutrients extracted, the duration, the rate and other parameters of extraction, and the distribution and proportions of the B-vitamins and other said nutrients in the extract. The species constituting said first plant matter are selected such as to get the desired nutrients in the extract in an optimum manner. The invention offers considerable latitude in the selection of the species that go into the first and second plant matters.

In the process of the present invention, the extraction of the nutrients from the said second plant matter will take place simultaneously during the extraction of the B-vitamins contained in the first plant matter. The nutrients of the second plant matter(s) may also undergo reaction with the said acidic components therein to a greater or lesser extent.

Thus, within the scope of the invention, the roles of said first and second plant matters are not mutually exclusive. The B vitamins, as also any of the other vitamins, minerals or other plant constituents that are desired to be extracted may come from the first plant matter(s) or from the second plant matter(s) or from both. Similarly, the acidic matter involved in the treating step of the process of the present invention may come from acidic constituents present in the said second plant matter(s) or partly from the first plant matter(s) and partly from said second plant matter(s).

Each of the first plant matter(s) and the second plant matter(s) may comprise a single plant species or a plurality thereof within the scope of the invention. The terms 'first plant matter(s)' and 'second plant matter(s)' have been used in the claims and description to convey the said scope. The forms 'first plant matter' and 'second plant matter' have been used at some places for convenience but it may be noted that the same scope is intended. This scope is intended wherever the term 'plant matter' appears herein.

Where said first plant matter and/or said second plant matter comprises a plurality of plant species, different combinations as regards the contacting steps within the treating step of the process of the present invention are possible. Different combinations offer different sets of benefits and advantages in view of the necessary processing parameters and costs, such as, for example, processing times, and the obtained yields.

The B vitamins and other nutrients contained in the second plant matter(s) undergo the same treatment as those in the first plant matter(s). Similarly, the said acidic matters present in both said first and second plant matters take part in said treatment of the B vitamins and nutrients present in both said plant matters.

As mentioned hereinabove, the roles of the first and second plant matters are not mutually exclusive, and they may play dual roles. Where the plant matters are in dual roles, the abovementioned selection considerations may be applied in respect of each of the plant species being considered whether forming part of the first plant matters or the second plant matters.

Within the scope of the invention, a first plant matter may additionally play the role of a second plant matter and vice versa. Both the first plant matter and the second plant matter may be in such dual roles within the scope of the invention.

Within the scope of the invention, options exist as regards the plant part to be taken up for extraction. Thus, each of the plant species selected as the first and/or second plant matters in the process of the invention may comprise any of the plant parts thereof, such as leaves, bark, fruits, flowers, seeds, branches, roots, rhizomes, others, or mixtures thereof. The choice will depend on their nutrient constituents and the forms in which the nutrient constituents are present, the acidic constituents, the extractability of the nutrient forms, the convertibility of the nutrient forms, cost considerations and other factors.

By selection of the appropriate source of the B vitamins, namely, the specie(s) constituting the first plant matter, and the appropriate organic acid(s) and other acidic compounds in the species constituting the second plant matter, it is possible to enhance the solubilities and therefore the extraction of the B vitamins while at the same time minimising the conversion of the non-vitamin B components that are not water-soluble into water-soluble forms.

In this way, an increase in the extraction of the B vitamins may be achieved in the process of the invention, and the processing times may be reduced.

Within the scope of the invention, the role played by the first and second plant matters may be a dual one. Each may function as a source for the desired B vitamins and other nutrients and also as a source of the organic acidic reacting compounds.

Thus, it is possible to select the first and second plant matters so as to generate synergies, cost benefits and other advantages. One such synergy, as mentioned hereinabove, is the enhancing of the extraction of the B vitamins while suppressing the extraction of other vitamin and mineral components that are not desired.

Within the scope of the invention, said first and second plant matter(s) may be dried and reduced in size for better contact when intermixed. Powdering the two plant matters is also an option. Alternatively, they may be converted into pulps and intermixed. A medium such as water may be used for enhancing the contact between the two plant matters. Thus, the two plant matters may be wetted with water or dispersed/slurried in water. Fluidisation and other means of contacting are also within the scope of the invention. Heating and pressure application to accelerate the treatment of the first plant matter with the second plant matter is within the scope of the invention.

As mentioned, the process of the invention offers a range of options as regards contacting the various species constituting the first and second plant matters carrying out the said treatment. The species of the first and second plant matters for said contacting and treatment may be taken up singly or collectively in groups. Such flexibility can be explored to generate processing advantages and cost benefits.

Thus, the process of the invention may offer mixtures that are ready for administration to subjects without the necessity of compounding operations such as admixing, homogenising, blending, sifting and the like. Such operations are optional finishing operations for the product. An administrable product in solution form may be obtained at the conclusion of the extraction step and in solid form by the simple step of evaporation of the solvent from the said solution. Compounding the product with one or more suitable excipients, binders and other additives to get a solid form extract product is within the scope of the invention. Agglomeration operations such as tabletting, pelletising and others on the solid form extract may be adopted if desired. Within the scope of the invention, the process of the invention may include a topping-up step to make the adjustments necessary to bring the mixture product of the invention into correspondence with the set of RDA figures or other such standards/specifications.

Thus, it is possible to obtain, by the process of the invention, an extract product that is substantially a specific combination of said B vitamins (and/or other said nutrients) and that has the desired proportions thereof. Such tailor-made extract compositions (products) reduce the cost of further processing thereof towards the making of formulations. They also make said further processing simpler and offer savings in energy, material and other costs. The selected proportions may be the RDA values or others.

The terms 'extract product' and 'extract' are used herein to refer to a solution of said nutrients in the solvent, namely water. The terms apply to extract solutions at any stage in the overall extraction process for extracting the B-vitamins and other nutrients from plant matter, and the terms also refer to the solution obtained at the completion of the extraction process. These terms are also used to refer to the product after any subsequent treatment of the extract, such as, for example, after solvent removal and after any downstream operations such as drying, crystallising, crushing, grinding, homogenising, pelletising, agglomerating and others. The water solvent is removed from said final solution at the completion of the said extraction process and this yields the extracted nutrients in a concentrated solution form or as a solid or semi-solid residue. The 'extract product' and 'extract' terms are also used to refer to said concentrated solution and the solid and semi-solid residues. The meaning appropriate to the context may be taken.

Any of the known drying processes may be adopted as required. In the embodiment described in detail hereinbelow, the concentrated solution containing the B vitamins is filtered and then subjected to a spray drying operation to yield the solid extract product. The adsorbed extract product is powdered and homogenised. Any other optional process operations such as filtration, size reduction, mixing, homogenising or others may be carried out as required within the scope of the invention.

The term 'extracted plant matter' is intended to refer to 'spent plant matter' resulting at any stage of the extraction process including at the completion of the process. The terms 'extracted plant matter', 'spent plant matter', 'spent matter' and 'residual plant matter' are used interchangeably. The term water solvent is intended for the purposes of this description and claims to cover within its scope not only pure (fresh) water but also dilute solutions of the said B vitamins and other nutrients in water. Thus, references in the claims to extraction of the plant matter by water also include extraction by water containing said B vitamins and other nutrients in solution. Such extract streams arise in multi-stage extractions. In such multi-stage extractions, material streams such as the dilute and rich extracts, spent matter and the fresh solvent can be organised in different patterns such as is known in the art. Different patterns offer different advantages and cost benefits in capital and operating costs.

The extraction thus results in a substantially ready-made B-vitamin composition that is a very convenient intermediate for processing into different dosage forms. Where adjustments are necessary in the component levels, topping by previously isolated B vitamin components may be carried out as part of the process of the invention.

It will be observed that the process provides considerable processing advantages and techno-economic benefits. In the prior art systems the nutrient components are extracted and isolated. Thereafter, the isolated nutrient components are admixed again to form the desired combination of the nutrients such as, for example, a formulation comprising a set of the B vitamins. The process of the invention makes redundant several operational steps and plant equipment required in the prior art procedures.

Thus, in one of the embodiments of the process of the invention for the extraction of the B group, the first plant matter comprises guava fruits, Holy basil leaves and lemon peels. The nutrients that are of interest therein and that are extracted by the process of the invention in the three components of the first and second plant matter mixtures are: B1, B2, B3, B5, B6, and B9 vitamins.

The second plant matter in this embodiment is also a mixture of different species. It comprises Holy basil leaves and lemon peels. The former contains several acid components such as oleanolic acid, ursolic acid, and rosmarinic acid while the latter contains citric and ascorbic acid. As mentioned, said plant matters may constitute both said first and second plant matters simultaneously within the scope of the invention. Within the scope of the invention, a said plant matter may constitute the nutrient(s) source or the source of said acidic compounds or both.

Within the scope of the invention, the operation of extraction may comprise a single stage or multiple stages. Many arrangements are possible as regards the number of stages, nature of extraction, routing and handling of the different extract and spent matter streams and the use thereof as product and/or as an extracting solvent, method of contacting of the solvent and material to be extracted, and the selection and adjustment of other process factors. Solvent removal may be adopted at any stage in the extraction or at the completion of extraction. Said solvent removal may be in one or more stages. Some of the said extract streams may be used as solvents for extraction of fresh or partly spent plant matter(s). All such possible variants of the process of the invention are within the scope thereof.

A number of known methods of carrying out the extraction step or the solvent removal step and other steps are known in the art. The process of the invention may adopt any of those or combinations thereof within the scope of the invention.

Within the scope of the invention, the administrable extract obtained by the process of the invention, a very suitable intermediate, may be converted into any of the known dosage forms and/or into any of the known pharmaceutical salts. Within the scope of the invention, the nutrients in the said administrable extract may be carried on any suitable pharmaceutically accepted carrier.

Within the scope of the invention, other operations may be carried out on the extract product of the invention, such as topping-up of constituents, adding of additional nutrients, converting into food, pharmaceutical or nutraceutical compositions, and admixing additives for colour, taste, texture, bulk, flavour, odour and others.

EXAMPLE

In order to provide a clearer understanding of the invention and without limitation to the scope thereof, an embodiment is described in detail hereinbelow.

The three plant matter components, guava fruits, holy basil leaves and lemon peels, were taken in the proportions of about 198:1:1 by wt.

Guava fruits were taken, and they were cleaned and washed in running water. Thereafter, the fruits were chopped in an SS chopper machine. The guava fruits were not dried, as drying tends to decompose the vitamin components in the fruit.

About 495 kg. of the chopped_(pulped) fruit was taken.

The holy basil leaves were taken and dried in open air under a shade. The dried material was ground in a swing hammer mill.

About 2.5 kg. of the dried leaf powder was taken.

The lemon peels were taken and also dried in the open air under a shade. The dried material was ground in a swing hammer mill.

About 2.5 kgs. of the dried lemon peel powder was taken.

The three materials were charged into an extractor which comprised an SS vessel of about 5000 L capacity provided with an agitator system and a steam jacket for heating the contents.

About 2000 L of water were charged into the extractor. The extractor was maintained at about 50 to about 65 C by heating with steam. The extraction was carried out for about 6 hours, during which period circulation of the solvent/extract was maintained. The extract was withdrawn from the bottom of the extractor and pumped to the top of the bed of plant material.

At the end of the extraction period the extract was drained from the extractor. About 1500 L of extract was obtained. This is referred to herein as the first extract batch.

The plant material bed was again extracted by charging about 2000 L of water, the other parameters being as in the first extraction. A batch of about 1500 L of extract was obtained from this extraction stage. This is referred to as the second extract batch.

The twice-extracted plant matter was subjected to a third stage of extraction. Again about 2000 L of water were charged. All other parameters were as in the first and second stage extractions. A batch of about 1500 L of extract was obtained. This is referred to as the third extract batch.

The said first and second batch extracts were individually concentrated at about 50 to about 65 deg. C down to a volume of about 150 L each. The two batches of concentrated extract were combined. This was the solution extract product of the invention.

The product extract was filtered in an SS Nutsche type filter using Hyflosupercel as filter aid.

The clear filtrate was subjected to spray drying in a SS spray drier at about 170 to 180 deg. C to give the extract product in the solid form.

The spray dried product was powdered in a SS multi-mill and sifted in a SS sifter to a particle size of about 40 to 80 mesh. The sifted material was blended in an octagonal blender for about one hour. About 40 to 50 kg. of dried powdered product was obtained.

The homogeneous powder product can be further processed by known processes to give formulations in the desired dosage forms.

The residual plant matter in the extractor after being subjected to three extractions was taken out and discarded.

The third batch extract was used to extract a batch of fresh plant matter.

The dried powdered product was analysed and the analysis is given hereinbelow.

In this embodiment, the treatment and extraction operations are carried out simultaneously in water medium. The first and second plant matters, after suitable preparation, are charged into an extractor vessel to which the water solvent is charged. The two plant matters are slurried in the water solvent by suitable agitation. The treatment reactions occur in the slurry medium. The extraction by dissolution of the B-vitamins and other nutrients, in their original forms and in their converted forms, into the water medium takes place substantially simultaneously with the treatment reactions.

As mentioned, guava fruits, holy basil leaves and lemon peels constitute the first plant matters in this example while the second plant matter comprises two components, holy basil leaves and lemon peels. The B vitamins present in guava fruits are B1, B2, B5, and B6; in holy basil leaves B3, and in lemon peels B9. The acidic compounds in holy basil leaves are oleanolic, ursolic and rosmarinic acids. The acidic constituents of lemon peels are citric and ascorbic acids.

Table I gives a comparison of the extract of the abovementioned embodiment of the invention with the required values and parameters. Column 2 of the table gives the desired specifications, and Column 3 gives the values obtained in the said extract of the embodiment. The quantities of the B-vitamins therein are in accordance with RDA requirements. The table indicates excellent correspondence of the said extract of the embodiment with the desired parameters, said correspondence being obtained in less processing time and with less processing steps than in the prior art processes.

TABLE I

Comparison of the extract of the embodiment of the invention with the required specifications.

| Physical Analysis | Specification | Actual Values | Testing method |
|---|---|---|---|
| Appearance and Color | Greyish Brown to Brown powder | Complies | Visual |
| Identification | Positive | Complies | HPTLC |
| Taste | Bitter & irony | Complies | Organoleptic |
| Odor | Characteristic | Complies | Organoleptic |
| Solubility | Soluble in water | Complies | USP XXIII |
| Loss on Drying | NMT 6% w/w | 3.3% | USP XXIII (IR) |
| Particle sizel | 98% min. thro' 20 mesh | 100% | USP XXIII |

| Assay of Actives | Specification | Result | Test Method |
|---|---|---|---|
| Vitamin B1 (Thiamin) | NLT 22 mg/g (2.2%) | 24 mg/g | HPLC |
| Vitamin B2 (Riboflavin) | NLT 20 mg/g (2%) | 22 mg/g | HPLC |
| Vitamin B3 (Niacin) | NLT 34 mg/g (3.4%) | 36 mg/g | HPLC |
| Vitamin B5 (Pantothenic acid) | NLT 38 mg/g (3.8%) | 40 mg/g | HPLC |
| Vitamin B6 (Pyridoxine | NLT 22 mg/g (2.2%) | 24 mg/g | HPLC |
| Vitamin B9 (Folic acid) | NLT 700 mcg/g (0.07%) | 755 mcg/g | HPLC |

| Microbiology | Specification | Result | Test Method |
|---|---|---|---|
| Total Plate Count | 1000 cfu/gram max | Complies | USP XXIII |
| Yeast and Mold | 100 cfu/g max | Complies | USP XXIII |
| Coliforms | Absent | Absent | USP XXIII |
| Salmonella | Absent | Absent | USP XXIII |
| E. coli | Absent | Absent | USP XXIII |
| Pseudomonas aeruginosa | Absent | Absent | USP XXIII |
| Staphylococcus aureus | Absent | Absent | USP XXIII |

| Chemical Impurities | Specification | Result | Test Method |
|---|---|---|---|
| Heavy Metals | NMT 10 ppm | Complies | USP XXIII |
| Arsenic as As | NMT 0.5 ppm | Less than 0.001 PPM | USP XXIII |
| Mercury as Hg | NMT 1 ppm | Less than 0.01 PPM | USP XXIII |
| Cadmium as Cd | NMT 1 ppm | Less than 0.01 PPM | USP XXIII |
| Lead as Pb | NMT 1 ppm | Less than 0.01 PPM | USP XXIII |
| Pesticides residue | Absent | Absent | USP XXIII |
| Remarks | The extract complies with the required specifications | | |

The process of the invention may be simply and easily adapted for batch, continuous or semi-continuous operation.

Embodiments and variations other than described hereinabove are feasible and may readily be carried out without undue experimentation by persons skilled in the art, and the same are within the scope and spirit of this invention.

Although the present invention has been described in considerable detail with reference to certain preferred versions thereof, other versions are possible. Therefore, the spirit and scope of the appended claims should not be limited to the description of the preferred versions contained herein.

While the invention has been described in connection with specific and preferred embodiments thereof, it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made. It should be appreciated that the scope of this invention is not limited to the detailed description of the invention hereinabove, which is intended merely to be illustrative, but rather comprehends the subject matter defined by the following claims.

What is claimed is:

1. A process for the extraction of B vitamins from guava fruit, holy basil leaf and lemon peel consisting essentially of:
treating guava fruit, holy basil leaf and lemon peel with one or more acidic compounds to convert the B-vitamins in the guava fruit, holy basil leaf, and lemon peel that are water-soluble into a form that is more water-soluble and/or to convert the B-vitamins in the guava fruit, holy basil leaf and lemon peel that are water-insoluble into a form that is water-soluble to form a mixture of guava fruit, holy basil leaf, lemon peel and the one or more acidic compounds; and
extracting the mixture of the guava fruit, holy basil leaf, lemon peel and the one or more acidic compounds with water or a dilute aqueous solution to yield an extract mixture of guava fruit, holy basil leaf, lemon peel and the one or more acidic compounds which contains the B vitamins, wherein the one or more acidic compounds are selected from the group consisting of acid(s) from Amla fruit, hydrochloric acid, sulfuric acid, nitric acid, phosphoric acid, succinic acid, citric acid, tartaric acid, acetic acid, ascorbic acid, oleanolic acid ursolic acid, rosmarinic acid and mixtures thereof.

2. The process of claim 1, wherein the one or more acidic compounds are derived from the mixture of guava fruit, holy basil leaf and lemon peel.

3. The process of claim 1, wherein the process involves more than one extraction.

4. The process of claim 1, wherein the guava fruit, holy basil leaf and lemon peel are subjected to one or more preparatory operations selected from the group consisting of washing, cleaning, dicing, cutting, drying, crushing, grinding, milling, screening and blanching.

5. The process of claim 1, wherein the water is removed from the guava fruit, holy basil leaf and lemon peel to yield a concentrated extract product.

6. The process of claim 5, wherein the concentrated extract product is dried to yield a solid form extract product and then subjecting the solid form extract product to at least one finishing operation selected from the group consisting of powdering, sieving, sifting, mixing and homogenizing.

7. A process for the extraction of B vitamins from guava fruit, holy basil leaf and lemon peel consisting essentially of:

treating a first mixture of guava fruit, holy basil leaf and lemon peel with one or more acidic compounds to form a second mixture of guava fruit, holy basil leaf, lemon peel and one or more acidic compounds, the one or more acidic compounds are selected from the group consisting of acid(s) from Amla fruit, hydrochloric acid, sulfuric acid, nitric, acid, phosphoric acid, succinic acid, citric acid, tartaric acid, acetic acid, ascorbic acid, oleanolic acid, ursolic acid, rosmarinic acid and mixtures thereof; and extracting the second mixture with water or a dilute aqueous solution to yield an extract mixture of guava fruit, holy basil leaf, lemon peel and one or more acidic compounds which contains the B vitamins.

8. The process of claim 1, wherein the treating step includes using the guava fruit, the holy basil leaf and the lemon peel in the respective, proportions of about 198:1:1 by weight.

9. The process of claim 7, wherein the one or more acidic compounds re selected to convert water-soluble B vitamins into more water-soluble forms or to convert water-insoluble vitamins into water-soluble forms.

10. The process of claim 7, wherein the one or more acidic compounds are selected to optimize the yield of B vitamins in the extract mixture.

11. The process of claim 7, wherein the one or more acidic compounds are selected to optimize the rates of extraction of the B vitamins.

* * * * *